US008353863B2

(12) United States Patent
Imran

(10) Patent No.: US 8,353,863 B2
(45) Date of Patent: Jan. 15, 2013

(54) SKIN PENETRATING DEVICE AND METHOD FOR SUBCUTANEOUS SOLID DRUG DELIVERY

(75) Inventor: Mir Imran, Los Altos Hills, CA (US)

(73) Assignee: InCube Labs, Inc., San Jose, CA (US)

( * ) Notice: Subject to any disclaimer, the term of this patent is extended or adjusted under 35 U.S.C. 154(b) by 0 days.

(21) Appl. No.: 12/705,529

(22) Filed: Feb. 12, 2010

(65) Prior Publication Data

US 2010/0204678 A1    Aug. 12, 2010

Related U.S. Application Data

(60) Provisional application No. 61/152,247, filed on Feb. 12, 2009.

(51) Int. Cl.
*A61M 31/00* (2006.01)
(52) U.S. Cl. ............... 604/57; 604/59; 604/60; 604/117
(58) Field of Classification Search .................. 604/511, 604/57, 58, 59, 60, 68, 72, 117, 61, 62, 63, 604/64; 119/605
See application file for complete search history.

(56) References Cited

U.S. PATENT DOCUMENTS

| 5,362,726 | A  | * | 11/1994 | Tackie et al. ............. 514/212.02 |
| 5,785,680 | A  | * | 7/1998  | Niezink et al. ................... 604/57 |
| 6,478,776 | B1 | * | 11/2002 | Rosenman et al. ...... 604/164.01 |
| 6,962,574 | B1 | * | 11/2005 | Noblitt et al. .................... 604/60 |
| 7,811,245 | B2 | * | 10/2010 | Kennedy, II ..................... 604/57 |
| 2003/0191449 | A1 |  | 10/2003 | Nash et al. |
| 2005/0202072 | A1 | * | 9/2005 | Buch-Rasmussen et al. 424/448 |
| 2005/0215991 | A1 |  | 9/2005 | Altman et al. |
| 2005/0251088 | A1 | * | 11/2005 | Kwon ............................. 604/60 |
| 2006/0094983 | A1 |  | 5/2006 | Burbank et al. |
| 2007/0123812 | A1 | * | 5/2007 | Pinchuk et al. ................... 604/8 |
| 2008/0033351 | A1 | * | 2/2008 | Trogden et al. ................. 604/57 |
| 2008/0058759 | A1 |  | 3/2008 | Makower et al. |
| 2009/0187167 | A1 | * | 7/2009 | Sexton et al. .............. 604/891.1 |

OTHER PUBLICATIONS

International Search Report, Written Opinion and Notice of Transmittal of same mailed Oct. 19, 2010 in International Application No. PCT/US2010/023965 15 pgs.

* cited by examiner

*Primary Examiner* — Bhisma Mehta
(74) *Attorney, Agent, or Firm* — Mahamedi Paradice Kreisman LLP

(57) ABSTRACT

Embodiments described herein provide a skin penetrating device and method for the subcutaneous delivery of therapeutic agents in solid form. One embodiment provides such a device comprising an elongated shaft having proximal and distal ends and a skin penetrating element detachably coupled to the shaft. At least a portion of the penetrating element is fabricated from a solid form therapeutic agent composition that dissolves in body tissue and is absorbed into the blood stream so as to produce a therapeutic effect. The penetrating element has shape for penetrating and lodging beneath the skin when inserted through the skin by force applied from the shaft. The penetrating element is configured to detach from the shaft when the shaft is pulled away from the skin so as to leave the element in place beneath the skin where it is absorbed by body tissue and the therapeutic agent is released.

35 Claims, 19 Drawing Sheets

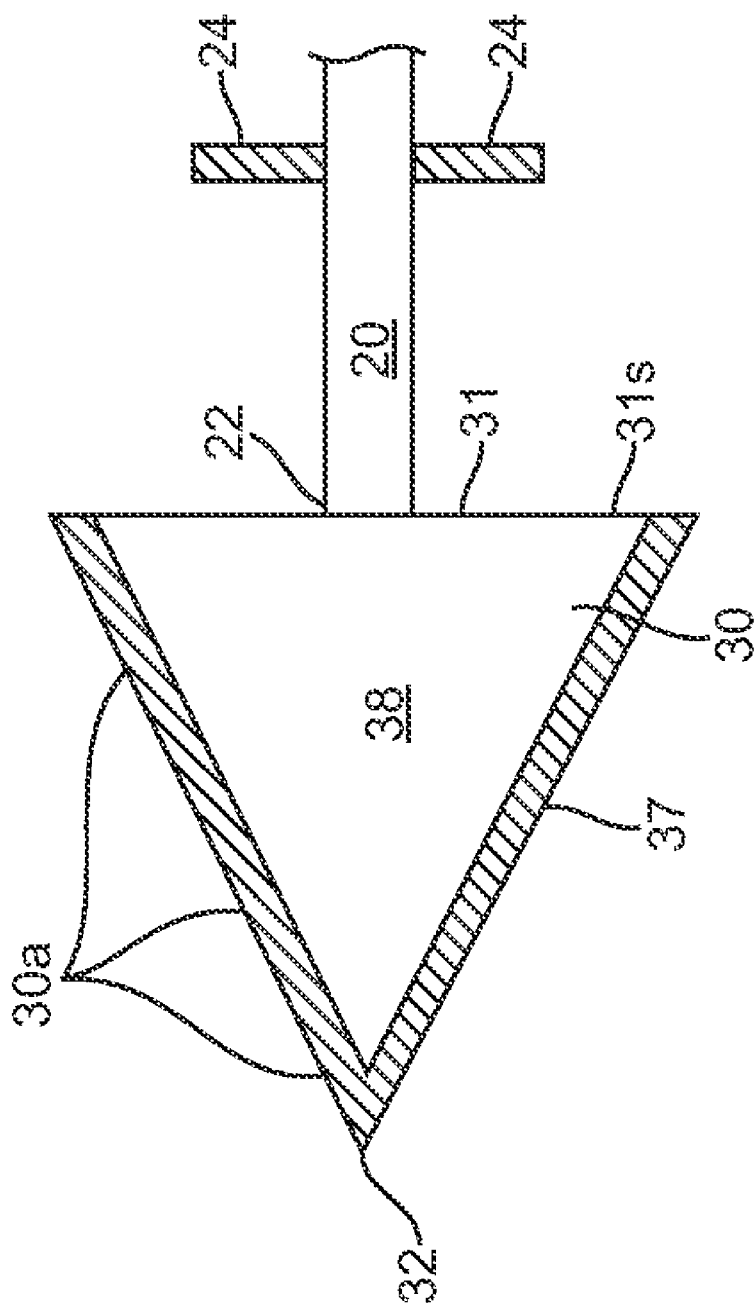

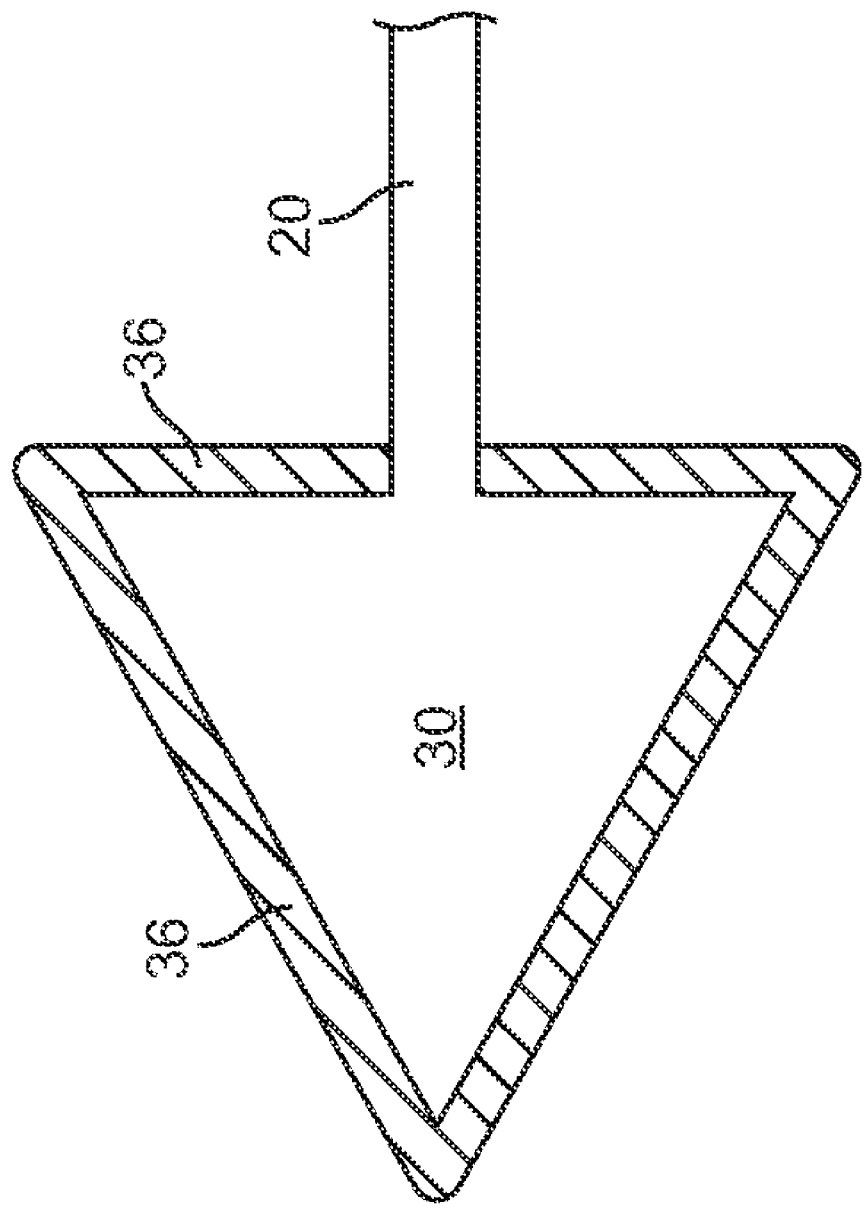

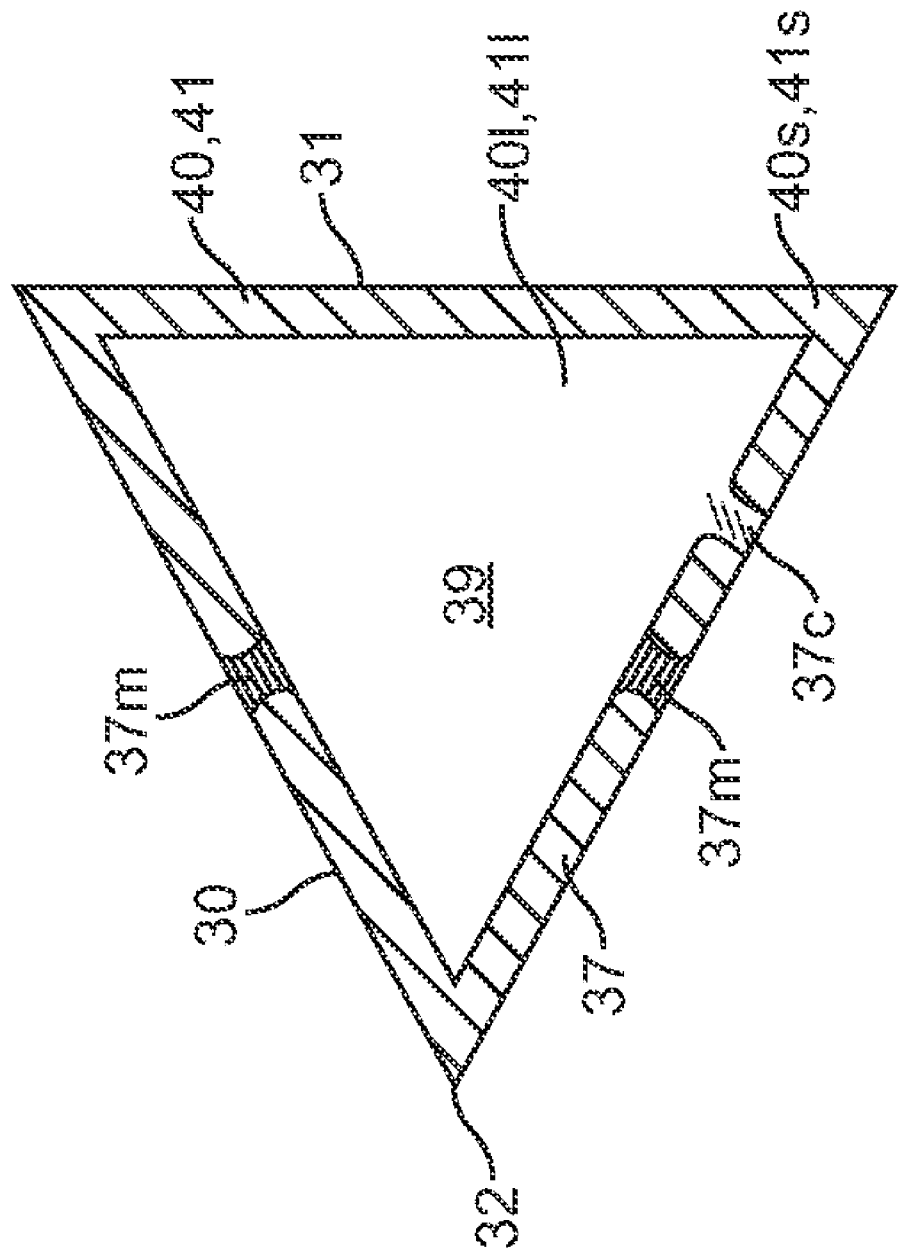

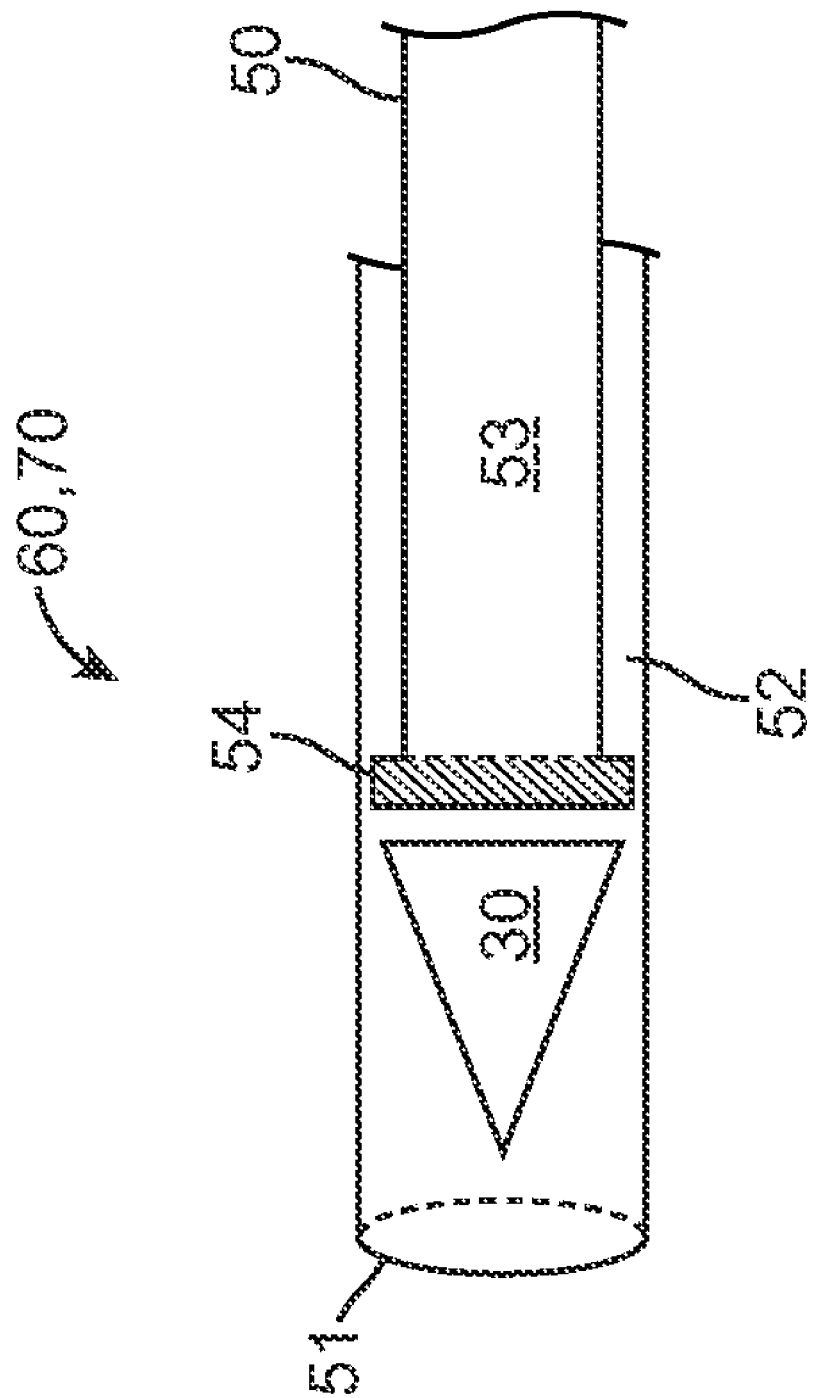

SKIN PENETRATING DEVICE AND METHOD FOR SUBCUTANEOUS SOLID DRUG DELIVERY

RELATED APPLICATIONS

This application claims the benefit of priority to Provisional U.S. Patent Application No. 61/152,247, entitled "Skin Penetrating Device and Method for Subcutaneous Solid Drug Delivery", filed Feb. 12, 2009; the aforementioned priority application being hereby incorporated herein by reference for all purposes.

FIELD OF THE INVENTION

Embodiments described herein relate to subcutaneous drug delivery. More specifically, embodiments described herein relate to a skin penetrating device and method for subcutaneous delivery of drugs in solid form.

BACKGROUND

Both oral and intravenous forms of drug delivery have a number of limitations. Oral delivery limitations include toxicity, poor absorption and varying concentrations over time. Intravenous limitations include the requirement to mix and store the drug in liquid form as well as the use of sterile technique. These can be particularly problematic in third world countries where adequate refrigeration and sterile needles are not readily available limiting shelf life and exposing the patient to infection. Thus, there is a need for improved methods of drug delivery which can extend shelf life and are more easily used in settings lacking refrigeration or sterile medical supplies.

BRIEF SUMMARY

Embodiments described herein provide a skin penetrating device, apparatus and method for the subcutaneous delivery of drugs and other therapeutic agents in solid form. Many embodiments provide a skin penetrating device that can subcutaneously deliver a selectable dose of a solid form therapeutic agent such as insulin which can be absorbed into the blood stream to produce a therapeutic effect for a selectable period of time.

One embodiment provides a skin penetrating device for the subcutaneous delivery of therapeutic agents in solid form comprising an elongated shaft having a proximal and distal end and a skin penetrating element detachably coupled to the distal end of the shaft. The skin penetrating element is fabricated from a solid form therapeutic agent composition that is configured to dissolve in body tissue fluids and be absorbed into the blood stream so as to produce a therapeutic effect, for example, a glucose regulating effect from an insulin compound. The penetrating element has an arrow head or other shape that is configured to penetrate and lodge beneath the skin of a patient when inserted through the skin by force applied from the shaft. This can be done by holding the shaft in the user's fingers and poking the skin or through means of a mechanism which advances the shaft into the skin such as a modified syringe plunger. In either case, when the tissue penetrating element is advanced into the skin and the shaft is pulled away from the skin, the tissue penetrating element detaches from the shaft and is retained beneath the skin typically, in a muscular layer. In one embodiment, detachment can be achieved by having a portion of the shaft inserted into a hole in the proximal end of the tissue penetrating element and held in place by an interference fit or adhesive with the force from pulling the shaft backwards away from the skin sufficient to cause detachment of the shaft from the tissue penetrating end. In another embodiment, the penetrating element can include an elongated section which inserts into a hole in the distal end of the shaft, with the release force being achieved by the act of pulling the shaft away from the skin. In various hand held embodiments, the shaft can include a finger grip or other gripping element positioned at a proximal portion of the shaft.

Typically, the tissue penetrating element will have a tapered shape with a pointed end such as an arrowhead shape. In these and related embodiments, the penetrating element can also have a flattened proximal surface so as to hold or retain the element in a selected tissue site in or beneath the skin when the shaft is pulled away by means of a normal force applied to an overlying tissue layer. Retention can also be facilitated through the use of one or more retaining features such as one or more barbs.

All or a portion of the tissue penetrating element can be fabricated from a solidly formed therapeutic agent composition which typically comprises the therapeutic agent and one or more pharmaceutical excipients such as binders, preservatives, disintegrants and time release agents. The excipients can also include hardening or binding agents configured to increase the hardness and thus tissue penetrating properties of the penetrating element. One or more of these excipients along with therapeutic agent can be micronized and then formed into the shape of the penetrating element using pharmaceutical manufacturing techniques known in the art. The penetrating element can be fabricated from a variety of drugs and other therapeutic agents including without limitation antibiotics, antibodies, proteins, insulin and other glucose regulating compounds, various chemotherapeutic agents, various vaccines, various hormones having birth control properties as well as combinations thereof. The amount of the therapeutic agent can be selected to achieve and maintain a selected plasma concentration of the selected therapeutic agent for a selected time period, for example between 6, 12 or 24 hours or even longer. This can also be facilitated by fabricating the penetrating element to degrade or break down at a selectable rate in the body through the use of one or more disintegrants. In this way, the penetrating element can maintain the plasma concentration of a selected therapeutic agent above a desired threshold for a selectable period of time.

In various embodiments of the invention, the tissue penetrating element can include a removable protective sheath to prevent accidental sticks and also to protect the therapeutic agent composition from oxidation and humidity. In many embodiments, the tissue penetrating element can comprise an outer layer or coating of non therapeutic material and an inner core containing the therapeutic agent composition. The outer layer can surround all or a portion of the inner core and is configured to degrade when exposed to the environment within the muscle or other subcutaneous tissue so as to expose the inner core. The outer layer can be formulated to perform one or more functions. These include serving as a barrier to gas and water vapor transmission to protect the inner core from oxidation and humidity and thus extend the shelf life of the therapeutic agent composition in a variety of ambient environments (e.g., tropical, dessert, etc.). The outer layer can also have a greater hardness than the inner core so as to increase the tissue penetrating properties of the tissue penetrating element. In related embodiments, the outer layer can comprise a hollow shell that is filled by a core or slug of therapeutic agent composition. Suitable materials for the outer coating or shell can include one or more sugars such as sucrose or other materials such as polyglycolic acid which are readily broken down by tissue fluids in muscle tissue or other subcutaneous tissue environments. The outer coating can also comprise one or more analgesics, anti-inflammatory and like agents to reduce any pain and swelling associated with implantation of the tissue penetrating element beneath the skin.

In another aspect of the invention, the tissue penetrating element can contain one or more liquid therapeutic agents that fill cavities formed in the tissue penetrating element. Similar to the mechanism for the absorption of solid embodiments, absorption of the outer layer of the penetrating element by body tissue fluids causes release of the inner liquid. The liquid therapeutic agent can be the same or a different agent as the agent compounded into the outer solid layers. In some embodiments, the liquid agent can comprise a compound which has a synergistic effect with or otherwise extends the pharmacologic half life of the therapeutic agent contained in the solid outer layers of the penetrating element.

Further details of these and other embodiments and aspects of the invention are described more fully below, with reference to the attached drawing figures.

BRIEF DESCRIPTION OF THE DRAWINGS

FIGS. 2a-2b are side views showing shapes of the tissue penetrating element. FIG. 2a illustrates an arrow head shape. FIG. 2b illustrates an elongated tapered shape as well as the use of barbs or other retaining elements.

FIG. 3a shows an embodiment where a distal end of the shaft is inserted into tissue penetrating element. FIG. 3b shows an embodiment where a proximal portion of the tissue penetrating element is inserted into the shaft.

FIG. 4 is a side view showing an embodiment of the tissue penetrating element having a removable sheath.

FIG. 5a-5c are side views showing embodiments of the tissue penetrating element having: i) an outer non therapeutic layer over a therapeutic composition core, (FIG. 5a); ii) a non-therapeutic hollow shell surrounding a therapeutic composition core (FIG. 5b); and iii) an outer layer with a fluid filled cavity (FIG. 5c).

FIGS. 6a-6c are side views illustrating use of a modified syringe as a mechanism for advancing the tissue penetrating element into the skin. FIG. 6a shows the entire syringe with the attached penetrating element; FIG. 6b shows the distal portion of the syringe and illustrates engagement of the syringe plunger with the penetrating element where only a portion of the penetrating element is positioned in the syringe; FIG. 6c shows engagement of the syringe plunger with the penetrating element where substantially all of the penetrating element is positioned in the syringe.

FIGS. 7a-7c illustrate the insertion of the penetrating element and shaft through skin and into subcutaneous tissue. FIG. 7c, illustrates use of stops to control the depth of penetration of the penetrating element. FIG. 7d illustrates detachment of the penetrating element from the shaft. FIG. 7e illustrates the penetrating element implanted in subcutaneous tissue with the shaft completely withdrawn.

DETAILED DESCRIPTION OF THE INVENTION

Figure 1:
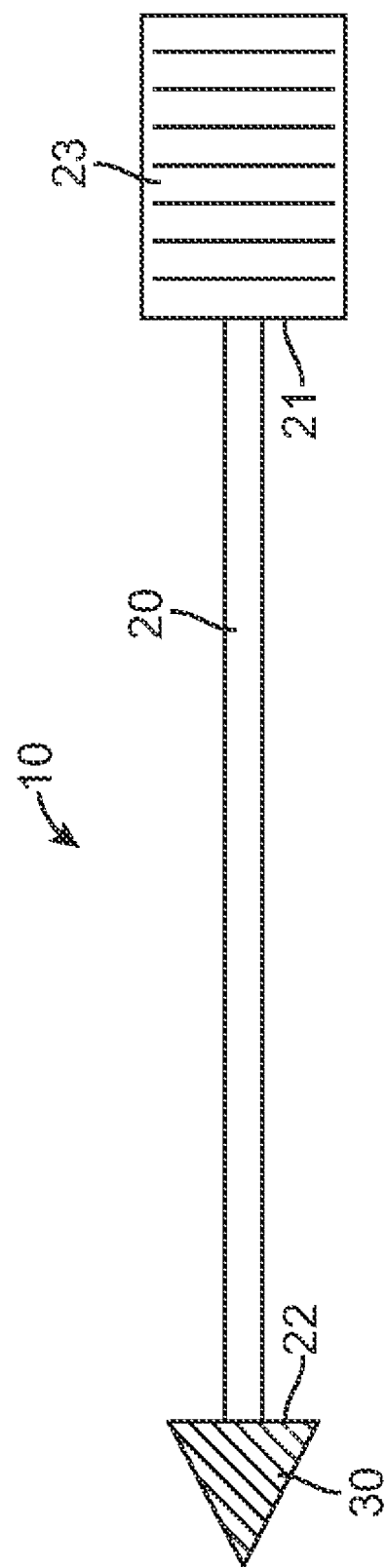
FIG. 1 is a side view of an embodiment of a skin penetrating device showing the shaft and tissue penetrating element.

Various embodiments described herein provide a skin penetrating device, apparatus and method for the subcutaneous delivery of drugs and other therapeutic agents in solid and/or liquid form. Many embodiments provide a skin penetrating device that can subcutaneously deliver a selectable dose of a solid form therapeutic agent which can be absorbed by the body into the blood stream to produce a therapeutic effect for a selectable period of time.

Referring now to FIGS. 1-6, one embodiment of a skin penetrating device 10 for the subcutaneous delivery of one or more solid form drugs or other therapeutic agents comprises an elongated shaft 20 having proximal and distal ends 21 and 22. The shaft can comprise a rigid metal or plastic known in the art and can be configured to be sterilized. In many embodiments, the shaft can include a cylindrical or other shaped finger grip 23 coupled to a proximal end of the shaft to allow a user to hold the shaft and deliver a penetrating element 30 (described below) beneath the patient's skin using a simple sticking motion. Shaft 20 can also include one or more stops or other depth control features 24 that are positioned on the shaft to control the depth of penetration of the penetrating element. Stops 24 can be fixed to shaft 20 or movably adjustable to allow the user to adjust the depth of penetration. In particular embodiments, shaft 20 can include markings or other indicia (not shown) for positioning of stops 24 to control the depth of penetration.

Figure 7A:
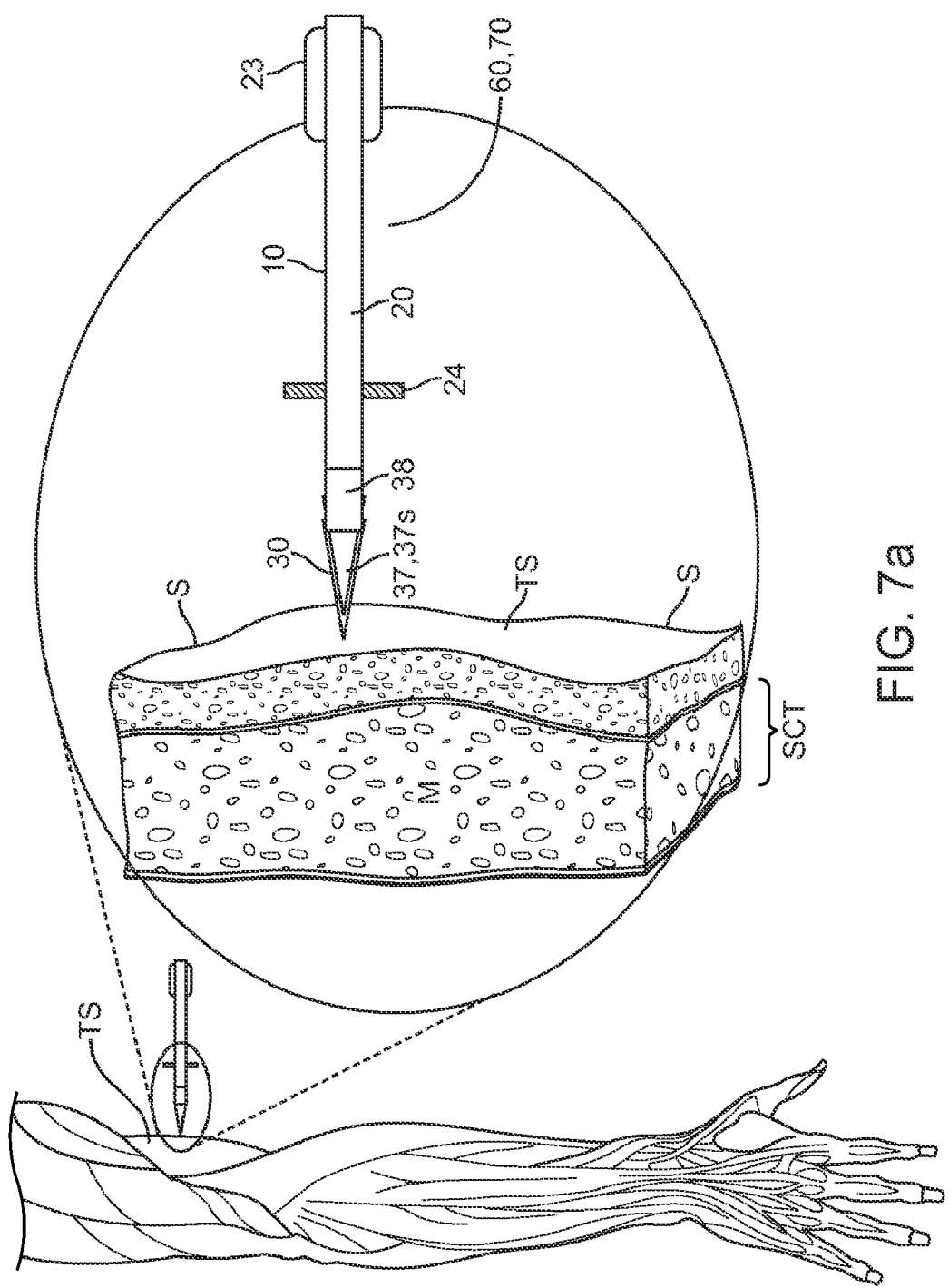
FIGS. 7a-7e are cross sectional views of the skin and subcutaneous tissue layers illustrating use of the skin penetrating device to penetrate and implant the tissue penetrating element into subcutaneous tissue.
Figure 7B:
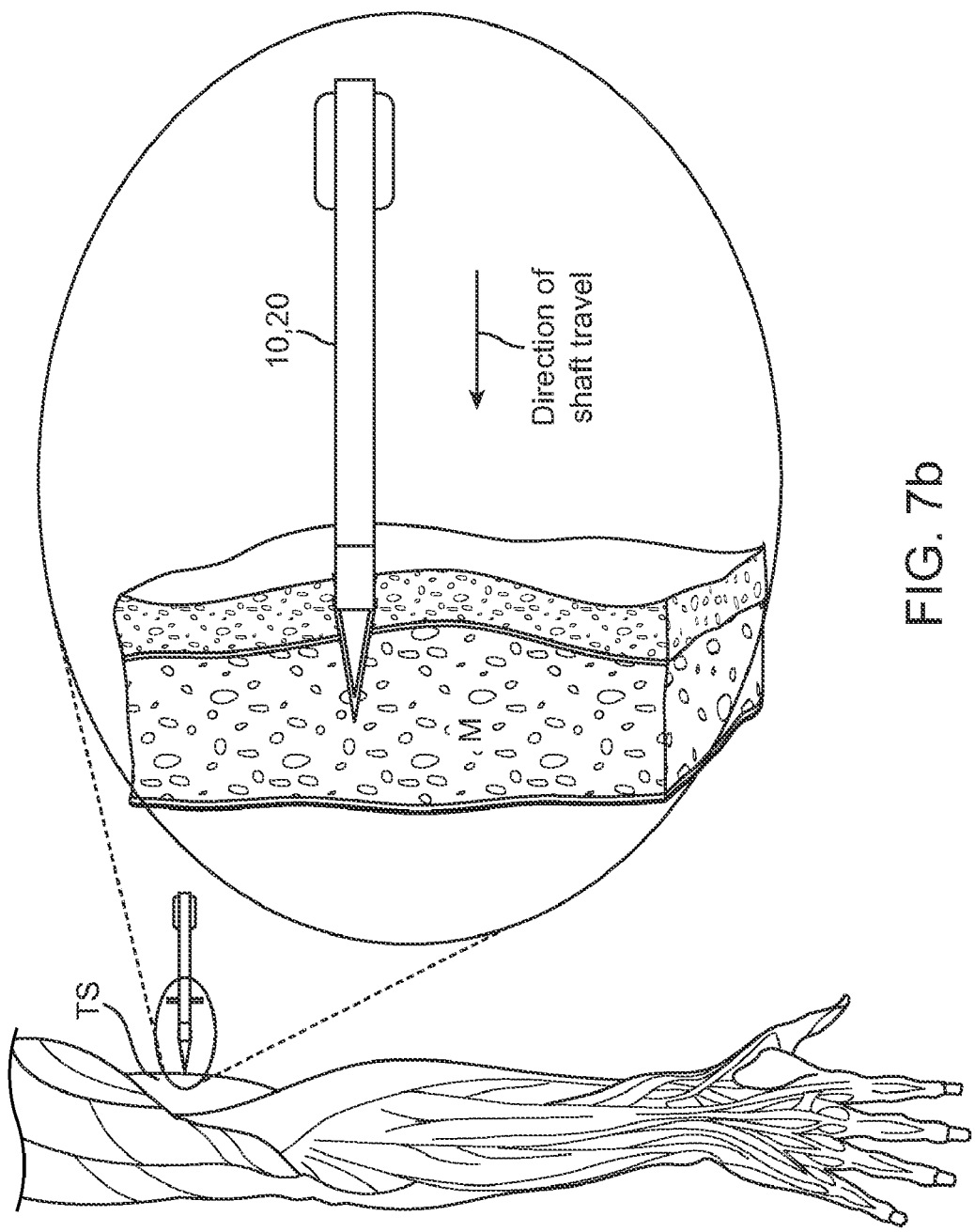

The distal end 22 of the shaft is detachably coupled to skin penetrating element 30. Penetrating element 30 has a proximal and distal end 31 and 32 and has a shape that is configured to penetrate and lodge beneath the skin S of a patient when inserted through the skin by force applied from the shaft (either by hand or through use of a mechanism). After lodging beneath the skin, the act of pulling the shaft away from skin causes the penetrating element to detach and remain beneath the skin S, the muscle M, or other subcutaneous tissue layer SCT (FIG. 7a). In various embodiments, the depth of penetration DP (FIG. 7c) of penetration element 30 can be controlled by the use of one or more stops 24 as well as the length and shape of the penetrating element.

Figure 2B:
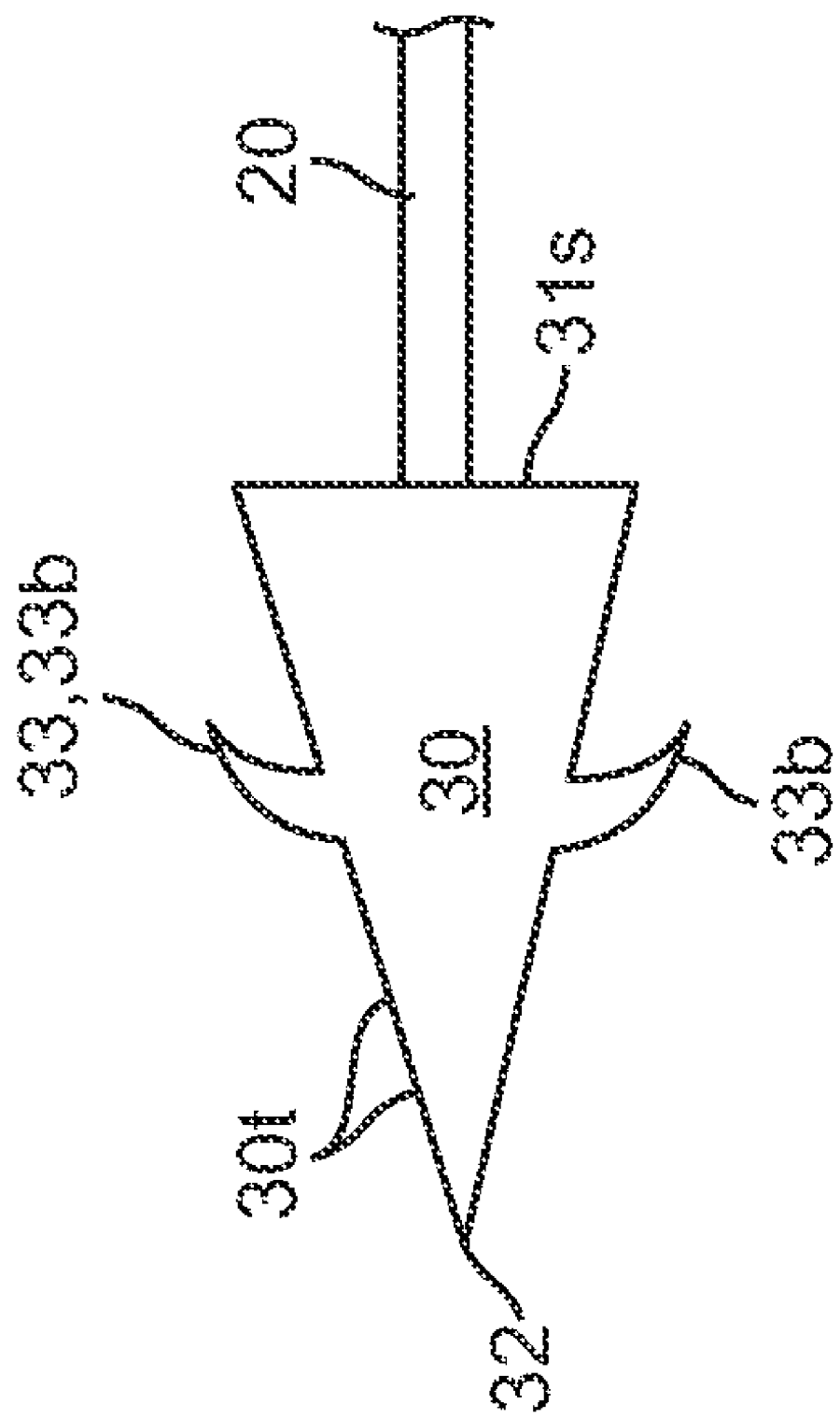
Figure 3A:
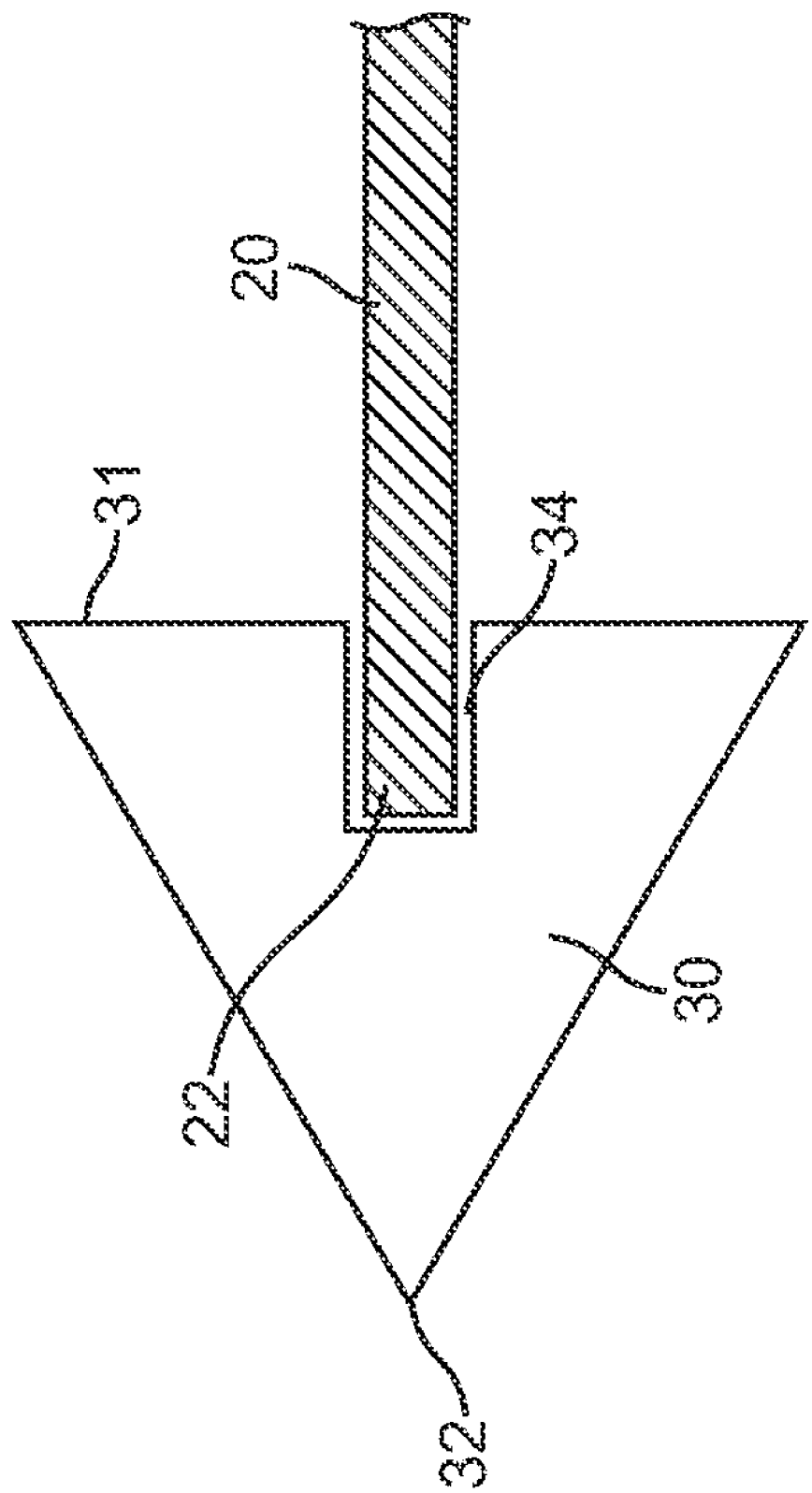
FIGS. 3a-3b are side views showing different configurations for coupling the tissue penetrating element to the shaft.
Figure 3B:
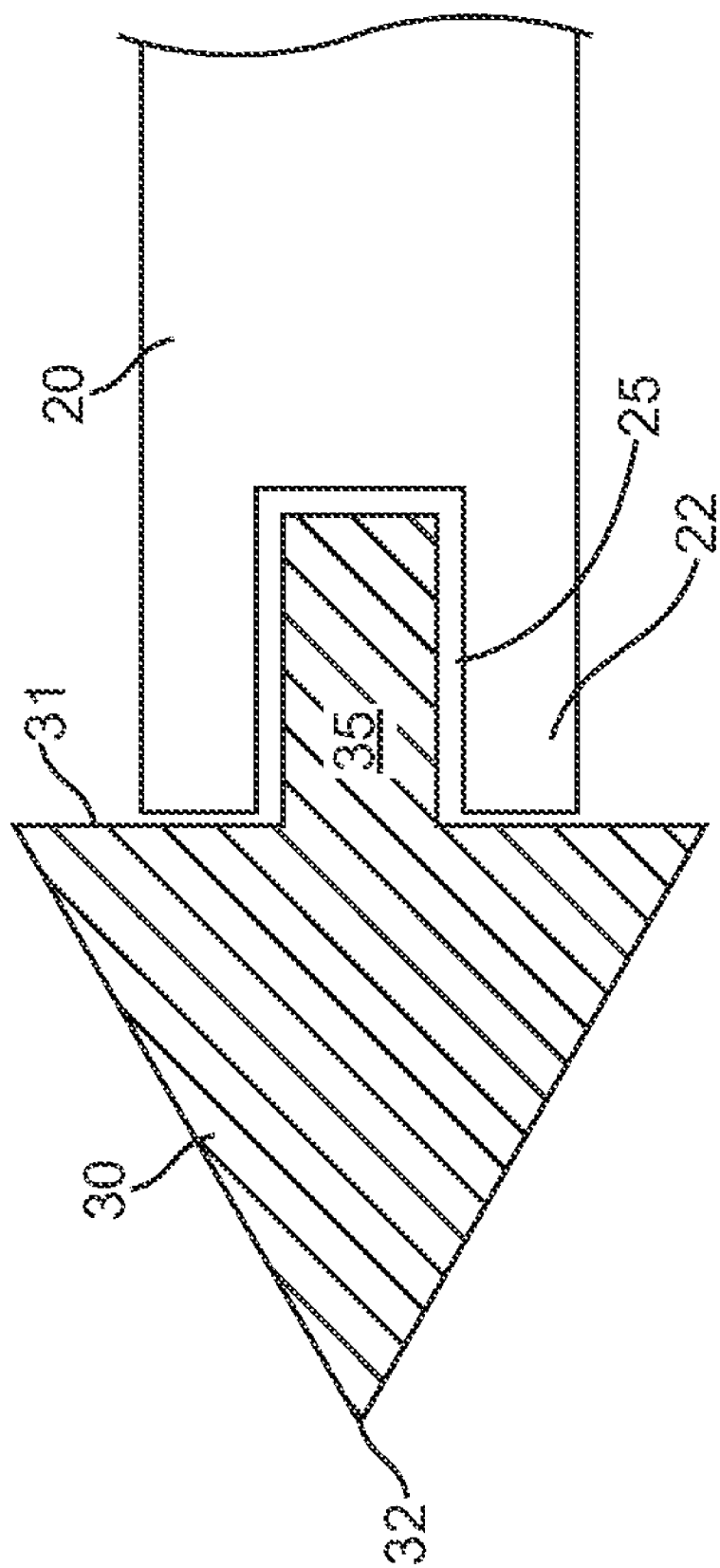

Typically, the tissue penetrating element 30 will have a tapered shape 30t with a pointed distal end such as an arrowhead shape 30a as shown in the embodiment of FIG. 2a. In these and related embodiments, the penetrating element can also have a flattened proximal surface 31s so as to hold or retain the element in a selected tissue site in or beneath the skin when the shaft is pulled away by means of a normal force applied to an overlying tissue layer. Retention can also be facilitated through the use of one or more retaining features 33 such as one or more barbs 33b as is shown in the embodiment of FIG. 2b.

Detachment of the penetration element from the shaft can be achieved through several different approaches. In one embodiment shown in FIG. 3a, detachment can be achieved by having a portion of the shaft inserted into a hole 34 in the proximal end of the tissue penetrating element 30 and held in place by an interference fit or adhesive with the force from pulling the shaft backwards away from the skin sufficient to cause detachment. In another embodiment shown in FIG. 3b, the penetrating element can include an elongated section 35 which inserts into a hole 25 in the distal end of the shaft, held in place by an interference fit or adhesive configured to release from the force of pulling the shaft away from the skin. In various embodiments, the release force of the adhesive or interference fit or other coupling can be configured to be in the range of 0.01 to 0.1 lbs. In still other embodiments, the penetrating element can be configured to be released by the act of twisting the shaft. This can be achieved through the use of a threaded coupling between the shaft and the penetrating element.

Tissue penetrating element 30 is typically fabricated from a solidly formed therapeutic agent composition 40 (FIGS. 5a-5c) which typically comprises the therapeutic agent 41 and one or more pharmaceutical excipients 42. As discussed herein, use of liquid form therapeutic agents is also contemplated. Suitable excipients 42 include binders, preservatives, disintegrants, anti-oxidants and time release agents. One or more of these excipients 42 along with therapeutic agent 41 can be solidified using methods such as crystallization and lyophilization and formed into the shape of element 30 using pharmaceutical manufacturing techniques known in the art, e.g. molding, compression, compaction, etc., or other pill forming methods. Additionally, all or portions of composition 40 can be micronized to facilitate break down and absorption of the therapeutic agent in the body. Also, various pharmaceutical methods can be employed to improve shelf life of the composition 40. Such methods can include lyophilization or other like freeze dried method to substantially remove all liquid water from the composition as well as through the use of one or more preservatives. Additional means for extending the shelf life of the composition can include use of a protective sheath and/or a protective coating for the penetrating element, embodiments of which are described herein. Depending on the composition, such methods can be use to achieve shelf lives from between 6 months to two years or longer.

The penetrating element 30 can be fabricated from a variety of drugs and other therapeutic agents 41. Such drugs and other therapeutic agents can include without limitation: antibiotics (e.g., penicillin, ampicillin, erythromycin, ciprofloxacin, vancomycin, etc.), antibodies, proteins, polypeptides, insulin and other glucose regulating compounds, various antidiarrheal drugs (e.g., Loperamide oxide) various chemotherapeutic agents (e.g., doxorubicin) various vaccines (e.g., diphtheria, cholera, tetanus, flu, measles and polio vaccines, vaccines can also be in the form of de-activated pathogens as well as antibodies), epinephrine and related compounds for treatment of allergic reactions and related conditions, various antiemetic compounds (e.g., 5-HT3 receptor antagonists such as those available under the tradename of ZOFRAN), various hormones having birth control properties (e.g., estrogen and progesterone as well as combinations thereof). The therapeutic agents can also include various pro-drugs which are metabolized into their active form once released into the body. Suitable pro-drugs can include anti-viral nucleoside analogs, lipid-lowering statins, antibody-directed/gene-directed enzyme pro-drugs for chemotherapy, etoposide phosphate, valganciclovir and fosamprenavir. Again, one or more of these drugs other therapeutic agents can be lyophilized including vaccines, antibodies, proteins and peptides.

In particular embodiments, one or more drugs, vaccines or other therapeutic agents 41 can be combined to yield a therapeutic composition that provides a combination therapy for treating multiple aspects of a particular disease or condition or group of conditions or to provide a battery of vaccines. For example, in one embodiment of a combination therapy for treating malaria, the therapeutic composition can comprise a combination of artemisinin with one or more partner drugs including mefloquine, lumfantrine or amodiaquine. Another embodiment of a combination therapy for malarial treatment can comprise quinine and tetra/doxycycline. In another embodiment of a combination therapy or regimen for treatment of schistosomiasis the therapeutic composition can comprise a combination of praziquantel, oxamniquine and metrifonat. In an embodiment of a combination vaccine for prevention of several child diseases, the therapeutic agent composition can include vaccines for one or more of the following diseases: Diphtheria, Tetanus and acellular Pertussis (DTaP), Hepatitis B and Polio virus (in inactive form).

The amount or dose of the therapeutic agent 41 in penetrating element 30 can be selected to achieve and maintain a selected plasma concentration of the particular therapeutic agent for a selected time period, for example between 6, 12 or 24 hours or even longer. Doses of the therapeutic agent can also be adjusted based on the weight range of the patient so various penetrating elements can be fabricated with a first dose for a first weight range (e.g., 100 to 150 lbs.) and another dose for a second weight range (e.g., 150 to 200) and so on. Doses can also be adjusted based on the condition of the patient (e.g., type I vs. type II diabetes, mild vs. severe diarrhea etc.) so that the penetrating element can be fabricated to have a first dose for a milder form of the disease and a second dose for a more severe form. Maintenance of plasma concentrations can be facilitated by fabricating the penetrating element to degrade or break down at a selectable rate in the body through the use of micronizing and/or one or more disintegrants known in the art. In this way, the penetrating element can maintain the plasma concentration of a selected therapeutic agent above a desired threshold level (e.g., a therapeutic threshold as is known in the art for the particular drug or other therapeutic agent or as determined using dose response curve methods) for a selectable period of time. In specific embodiments, the therapeutic agent composition 40 is configured to dissolve at a substantially constant rate. In various alternative embodiments, secondary delivery means can also be used to further control the release rate of therapeutic agent such as incorporating the therapeutic agent into liposomes or other like structure which are later broken down in the blood stream or other selected site in the body to release the therapeutic agent.

In various embodiments, the tissue penetrating element 30 can include a removable protective sheath 36 to prevent accidental sticks and also to protect the therapeutic agent composition from oxidation and humidity. Sheath 36 can comprise various resilient polymers known in the art configured to have gas/water vapor barrier properties and can be configured to be pulled off or torn away. In addition or as an alternative to protective sheath 36, the entire device 10 can be packed in sterile protective packaging (not shown) which in various embodiments can comprise band-aid-like packaging, or tubular sheath that fits over the entire device including shaft 20. The packaging can include various identifying indicia including the type and dose of therapeutic agent as well as the expiration date. Such packaging can also be substantially airtight so as to extend the shelf life of the therapeutic agent.

In many embodiments, the tissue penetrating element 30 can comprise an outer layer or coating 37 and an inner core 38 containing the therapeutic agent composition (as used herein, coating and layer are considered interchangeable, though the coating 37 can be produced by a coating method). Outer layer 37 can surround all or a portion of the inner core 38 and is configured to degrade when exposed to the body fluids within the subcutaneous tissue layers (e.g., muscle, fascia, etc.) so as to expose the inner core. The outer layer 37 can be formulated to perform one or more functions. These include serving as a barrier to gas and water vapor transmission to protect the inner core from oxidation and humidity and thus extend the shelf life of the therapeutic agent composition 41 in a variety of ambient environments (e.g., tropical, dessert, etc.). The outer layer can also have a greater hardness than the inner core so as to increase the tissue penetrating properties of the tissue penetrating element. Suitable materials for the outer layer can include one or more sugars such as sucrose or other materials such as polyglycolic acid (PGA), polylactic-co-glycolic acid (PLGA), or like material which are configured to be broken down by tissue fluids in the subcutaneous tissue environment (e.g., by hydrolytic degradation). The outer coating 37 can also comprise one or more analgesics, anti-inflammatory and like agents to reduce any pain and swelling associated with implantation of the tissue penetrating element beneath the skin.

Figure 5A:
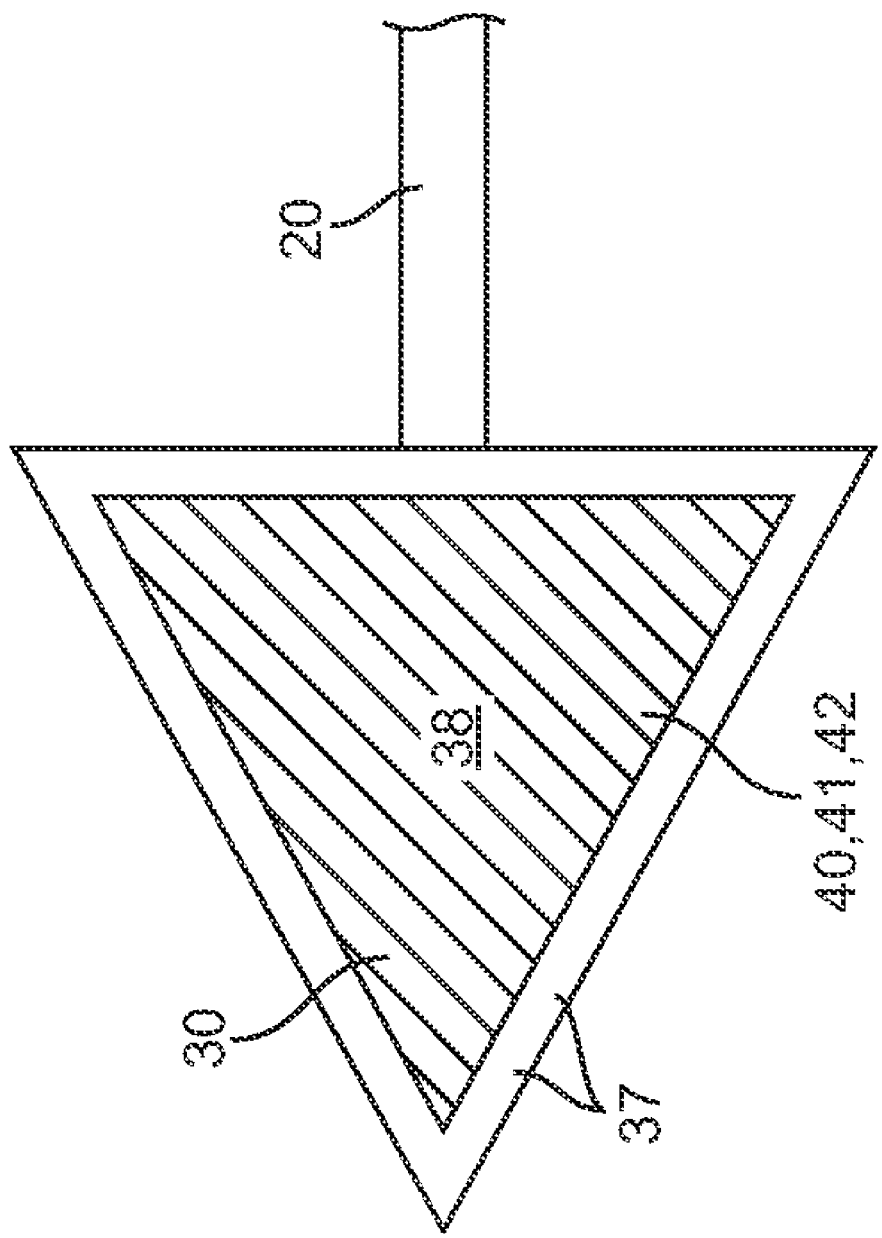
Figure 5B:
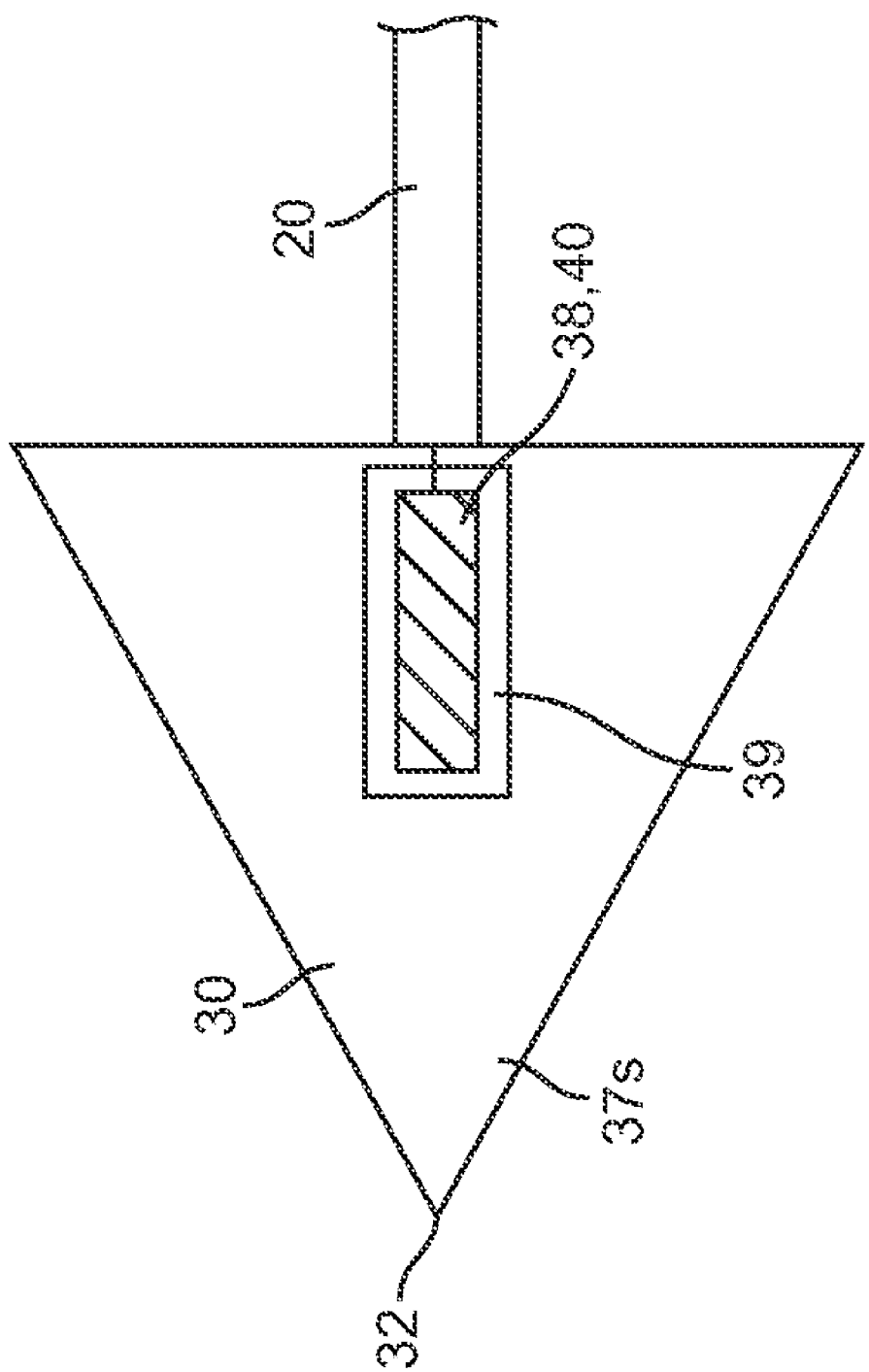

In some embodiments, outer layer 37 can comprise a shell 37s with a cavity 39 filled by a core 38 of therapeutic agent composition 40 as shown in FIG. 5b. The core 38 may be comprised of one or more pellets, or be pelletized. The shell 37s can have an arrow head, bullet or other tissue penetrating shape with sufficient flexural rigidity to penetrate the skin into subcutaneous tissue. In these and related embodiments, shell 37s and core 38 can be fabricated separately and then assembled. Similar to coating 37, shell 37s can be fabricated from materials such as PGA or PGLA that are configured to be degraded in the subcutaneous tissue environment so as to expose core 38.

In another aspect of the invention, the tissue penetrating element 30 can contain a liquid therapeutic agent composition 40l including a liquid form therapeutic agent 41l that fill cavities 39 formed in the tissue penetrating element as is shown in FIG. 5c. Similar to the mechanism for the absorption of solid form agent embodiments, absorption of the outer layer 37 of the penetrating element by body tissue fluids causes release of the inner liquid 40l. In these and related embodiments, layer 37 can include a solid form therapeutic composition 40s including a therapeutic agent 41s. The liquid therapeutic agent 41l can be the same or a different agent as the solid agent 41s compounded into the outer solid layer 37. In some embodiments, the liquid agent 41l can comprise a compound which has a synergistic effect with or otherwise extends the pharmacologic half life of the therapeutic agent 41s contained in the solid outer layers 37 of the penetrating element 30.

Also, in these and related embodiments having liquid filled cavities 39, layers 37 can have modified sections 37m that are thinner walled or otherwise pre-stressed or constructed from materials having a lower tensile strength such that the compression or other forces imparted on penetrating element 30 during penetration into the subcutaneous tissue causes a channel 37c to open in layer 37 after insertion (either immediately or soon afterwards due to more rapid breakdown of sections 37m from body tissue fluids). Such embodiments allow for the rapid release of liquid therapeutic agent composition 40l through channels 37c soon after placement of the penetrating element in subcutaneous tissue layer SCT and in turn, for the rapid release of liquid therapeutic agent 40s into the blood stream. Use of modified sections 37m can also be employed on all solid embodiments of penetrating element 30 so as to provide channels 37c for the infiltration of body fluids (e.g., interstitial fluids, blood, lymph, etc.) into the interior of the penetrating element and thus, the faster and/or enhanced breakdown and release of therapeutic agent 41 into tissue and the blood stream.

Figure 6A:
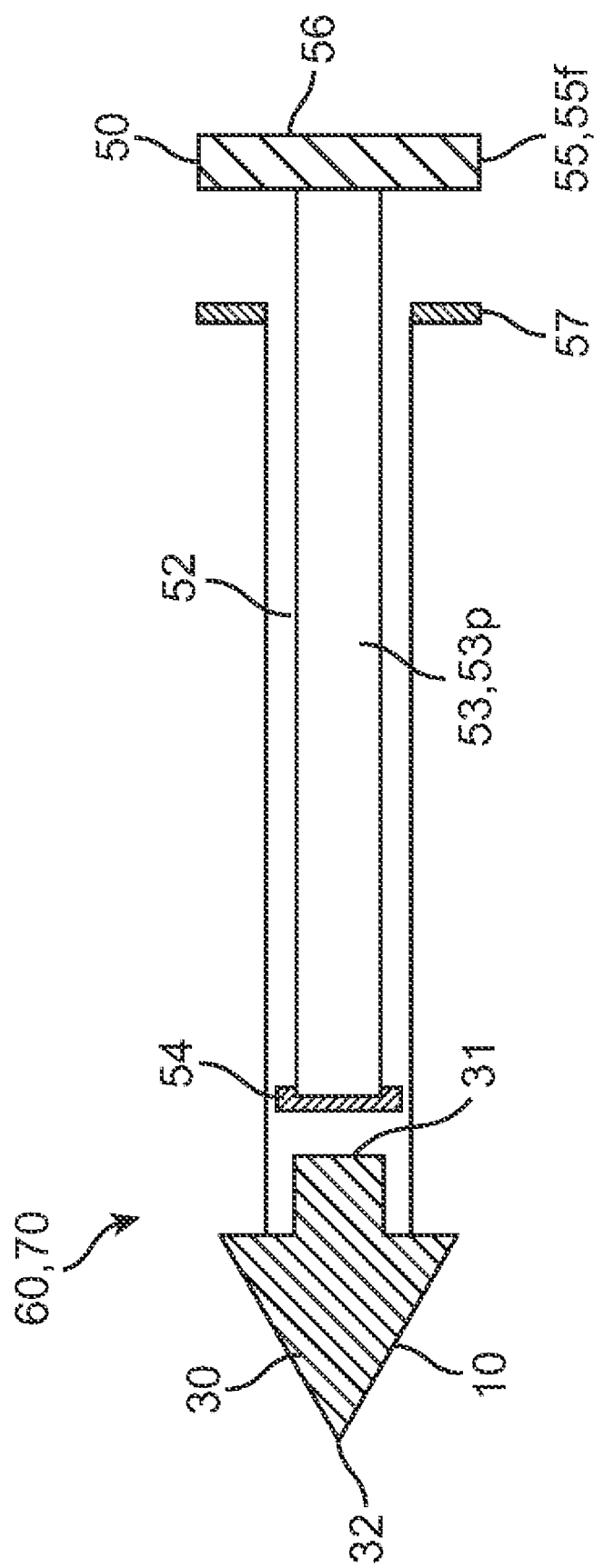
Figure 6B:
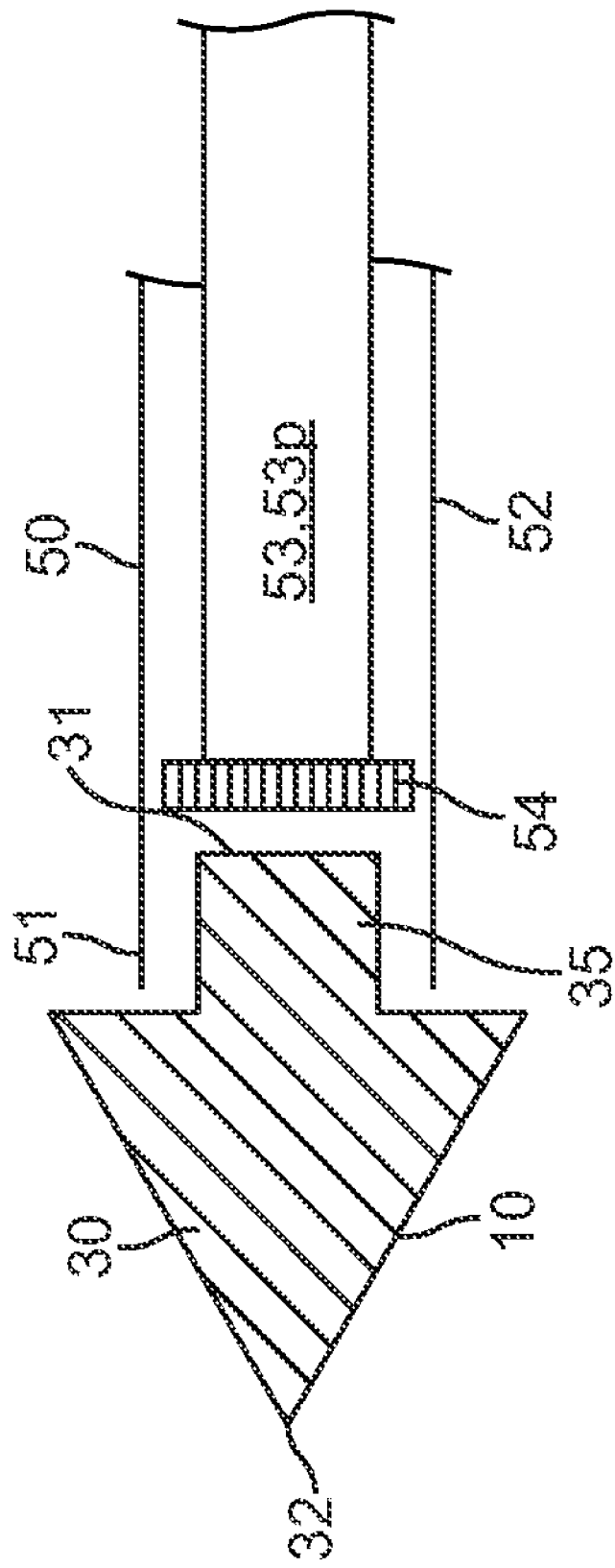

Referring now to FIGS. 6a-6c, in various embodiments device 10 can be configured to be advanced by a mechanism 50 that engages with penetrating element 30. In these and related embodiments device 10 and mechanism 50 can comprise an apparatus 60 or system 70. In particular embodiments, mechanism 50 can correspond to a syringe 50 with the penetrating element 30 attached to the distal end 51 of the syringe with the distal end of the penetrating element projecting from barrel 52 as is shown in FIGS. 6a and 6b. In other embodiments, substantially all of the penetrating element 30 can be positioned within syringe barrel 52. The syringe includes a modified syringe plunger 53 having a pusher plate 54 so as to act as a piston 53p that travels within barrel 52 and pushes or otherwise engages the proximal end 31 of penetrating element 30 so as to force the penetrating element off and/or out of the distal end 51 of the syringe 50 and through the skin and into the muscle or other subcutaneous tissue layer. The depth of penetration can be controlled by selection of the length of plunger 53 and a stop feature 55, such as a flange 55f on the proximal end 56 of the plunger which can an engage a corresponding stop feature 57 on the syringe barrel. In alternative embodiments, plunger 53/pusher plate 54 need not directly engage the penetrating element, but rather can eject the penetrating element using the force of compressed air from depressing the plunger. In still other embodiments, the plunger can engage a spring (not shown) positioned within the barrel that in turn engages the proximal end 31 of the tissue penetrating element. Use of such a spring allows a substantially constant amount of force to be applied to the penetrating element so as to control the depth of penetration.

Referring now to FIGS. 7a-7e, an exemplary embodiment of a method of using device 10 and apparatus 60/system 70 will now be presented. In this embodiment, the penetrating element comprises a shell 37s and core 38; however, it will be appreciated that use of this or similar methods are equally applicable to other embodiments of the penetrating element discussed herein. Also, these or similar methods are also applicable to the use of an advancement mechanism 50 described herein.

Figure 7C:
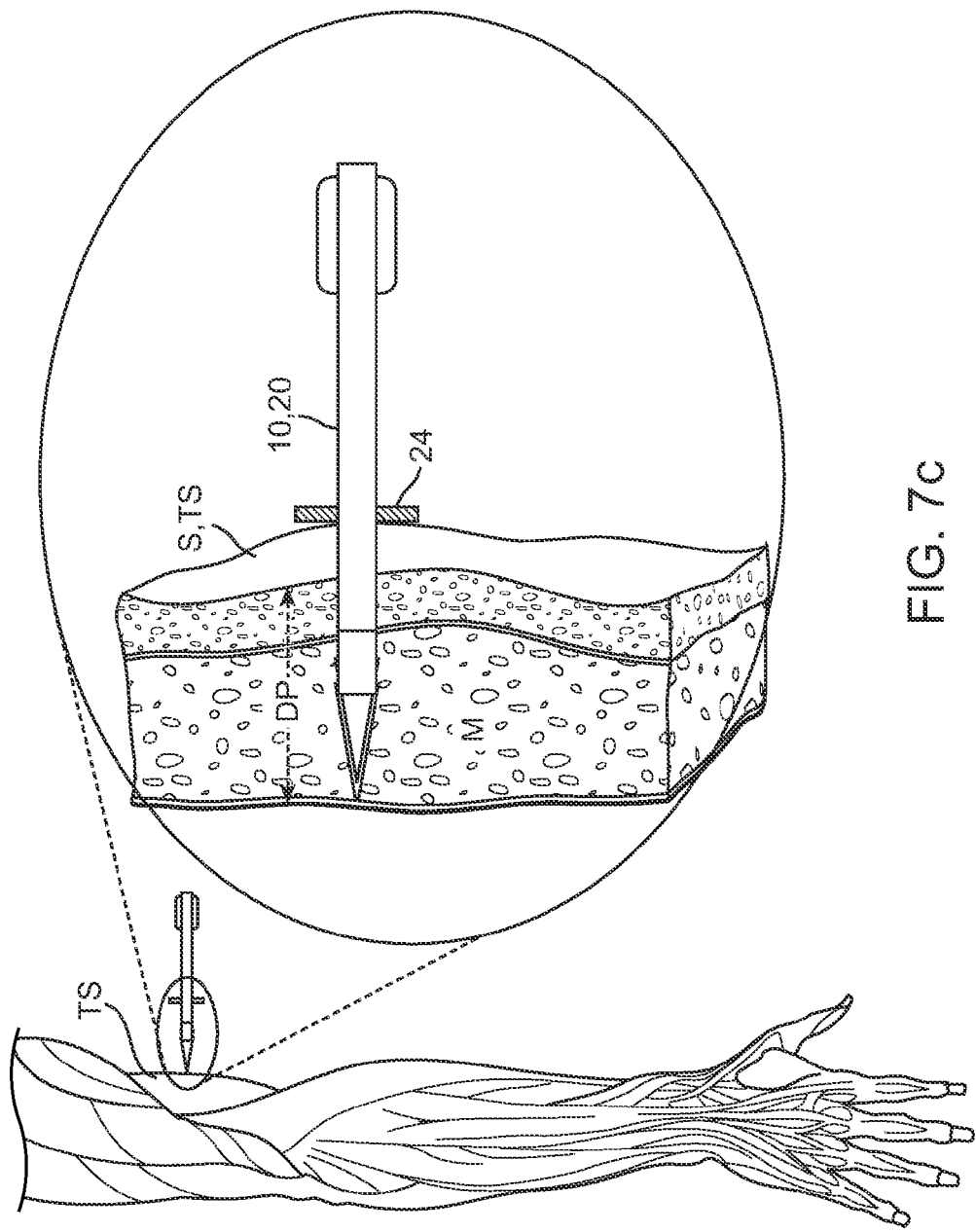
Figure 7D:
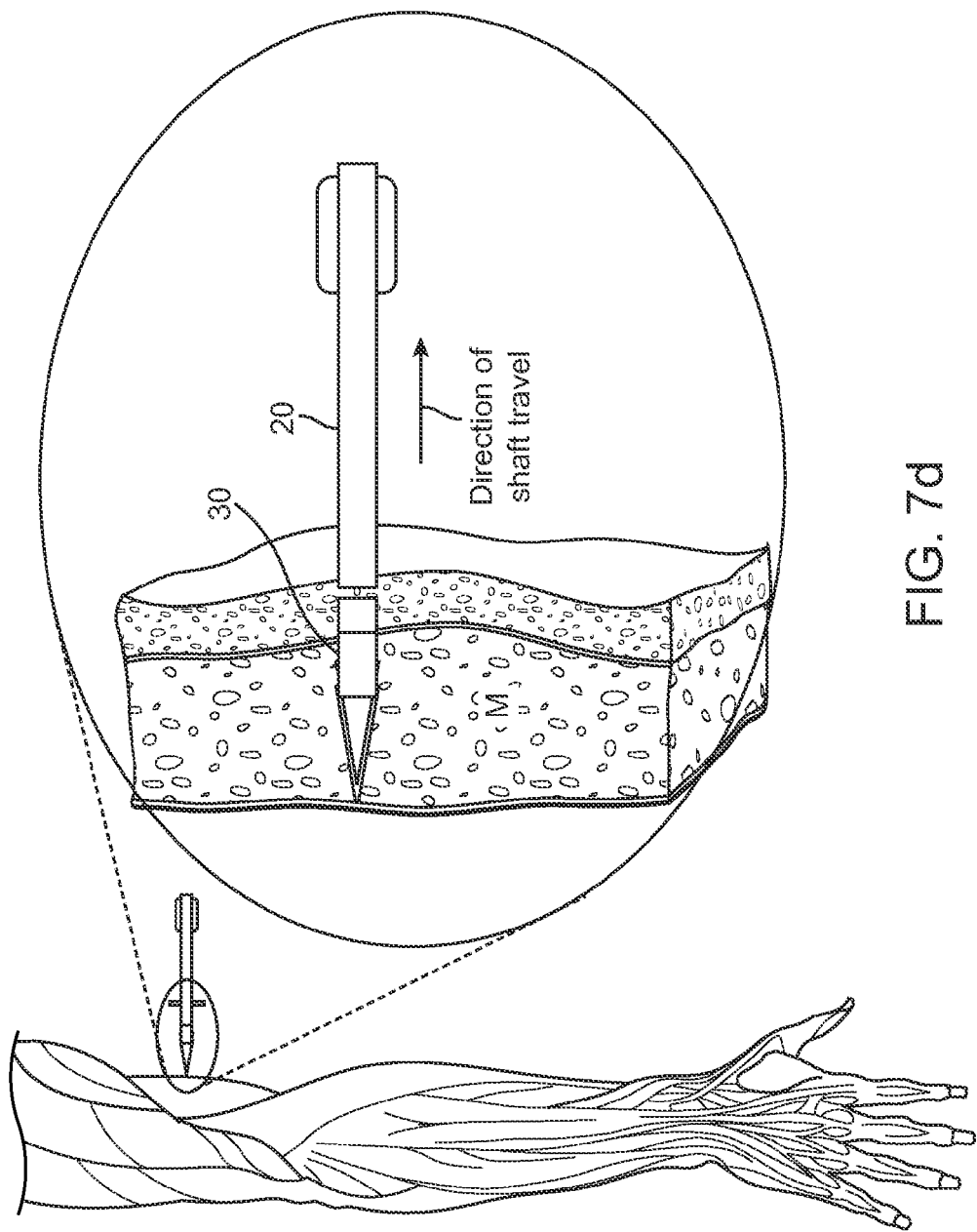
Figure 7E:
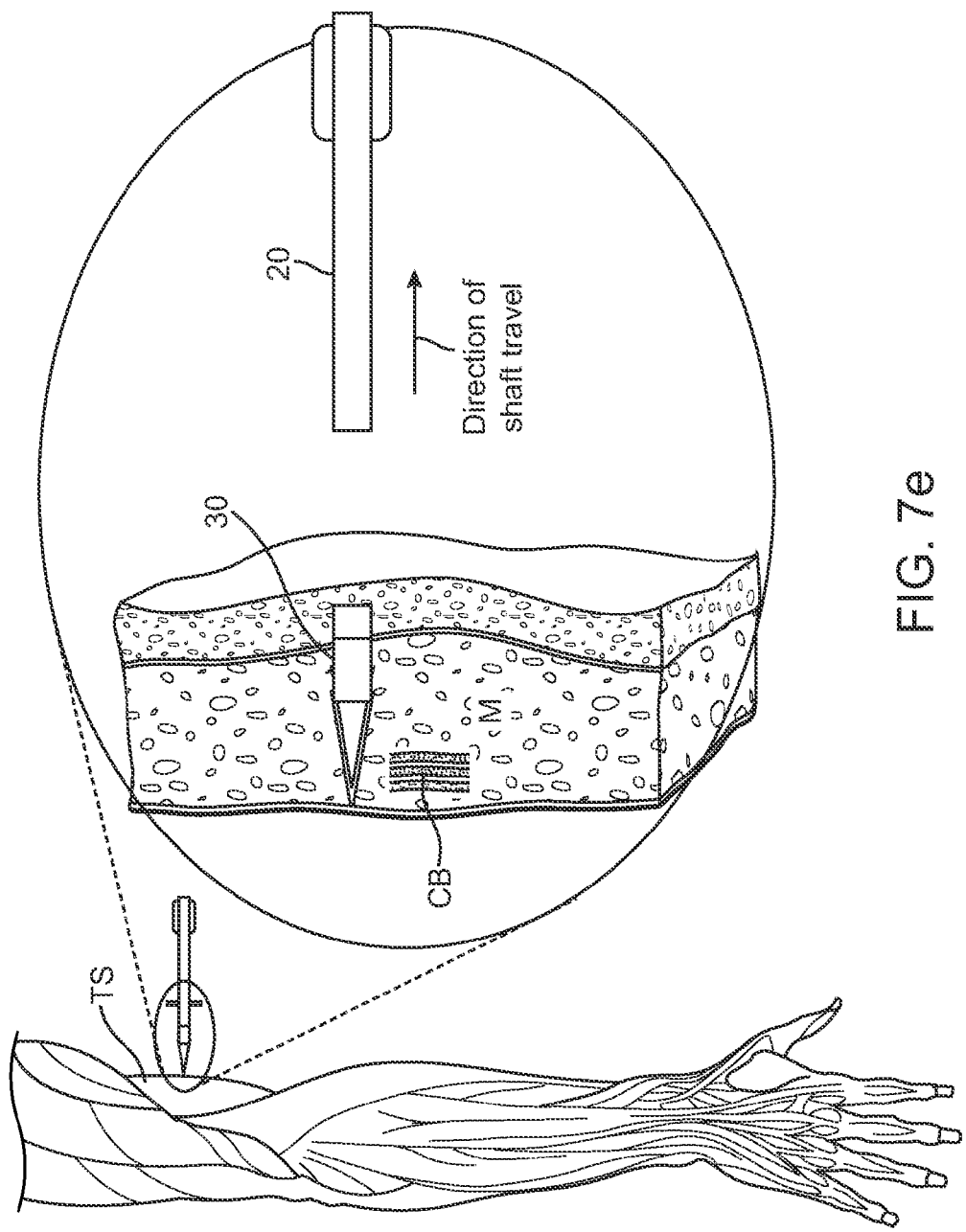

Grasping shaft 20 using the fingers, the user pokes or sticks the penetrating element through the skin S at a selected tissue site TS and into subcutaneous tissue layer SCT which will typically be a muscular layer M. Tissue site, TS will typically comprise an arm, thigh or buttocks such that there is a substantial thickness of muscle tissue underneath the skin. The depth of penetration DP into tissue can be controlled by the use of one or more stops 24 positioned on shaft 20 (as is shown in FIG. 7c) as well as the size and shape of the penetrating element. Once the penetrating element is inserted into the subcutaneous tissue, the user pulls back the shaft away from the skin which causes the penetrating element to detach from the shaft (as is shown in FIG. 7d) leaving the penetrating element 30 in place in the muscle M or other subcutaneous tissue layer as is shown in FIG. 7e. Once so placed, interstitial fluids in the muscle tissue break down outer layer 37/shell 37s causing core 38 to be exposed which is itself broken down and absorbed into the interstitial fluids and then into capillary beds CB within the muscle tissue and ultimately into the blood stream where it is distributed through the body.

Figure 8:
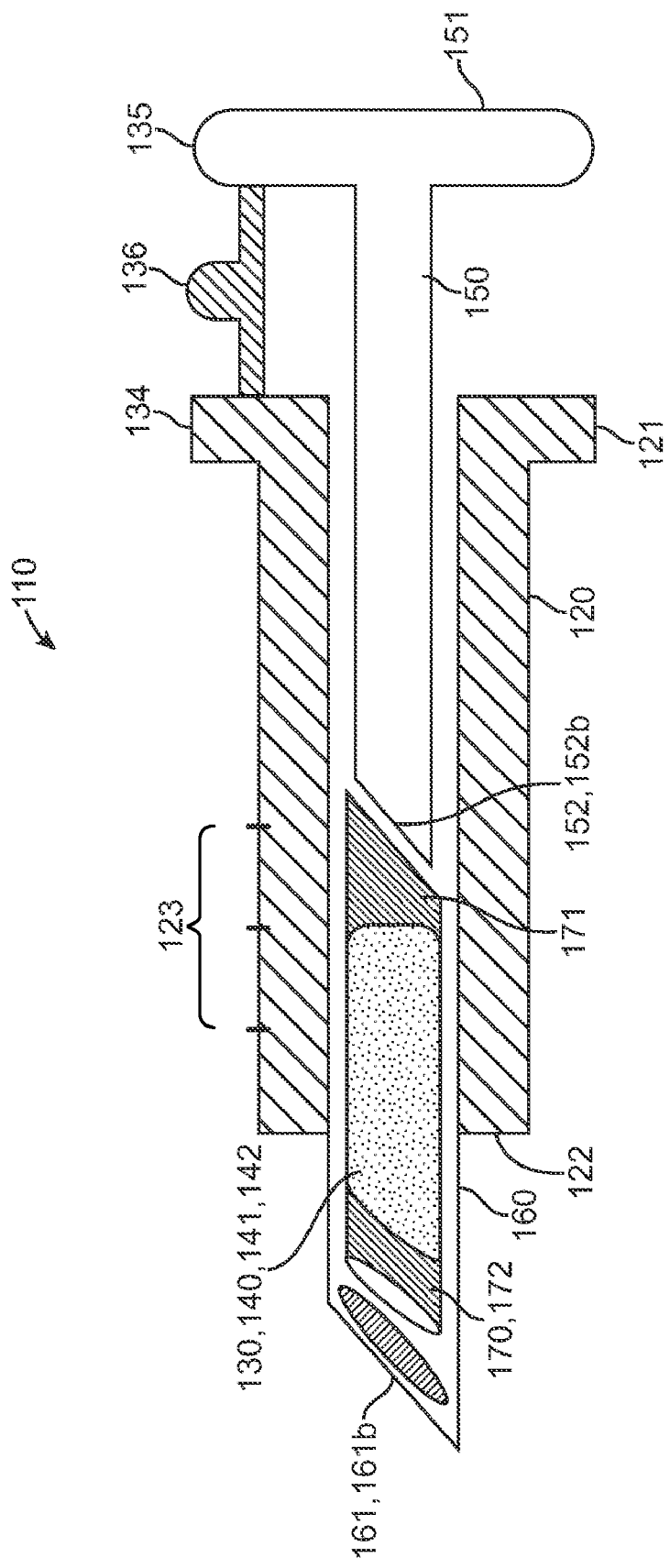
FIG. 8 is a side view illustrating an embodiment of a syringe device for delivering a solid form therapeutic agent composition.
Figure 9:
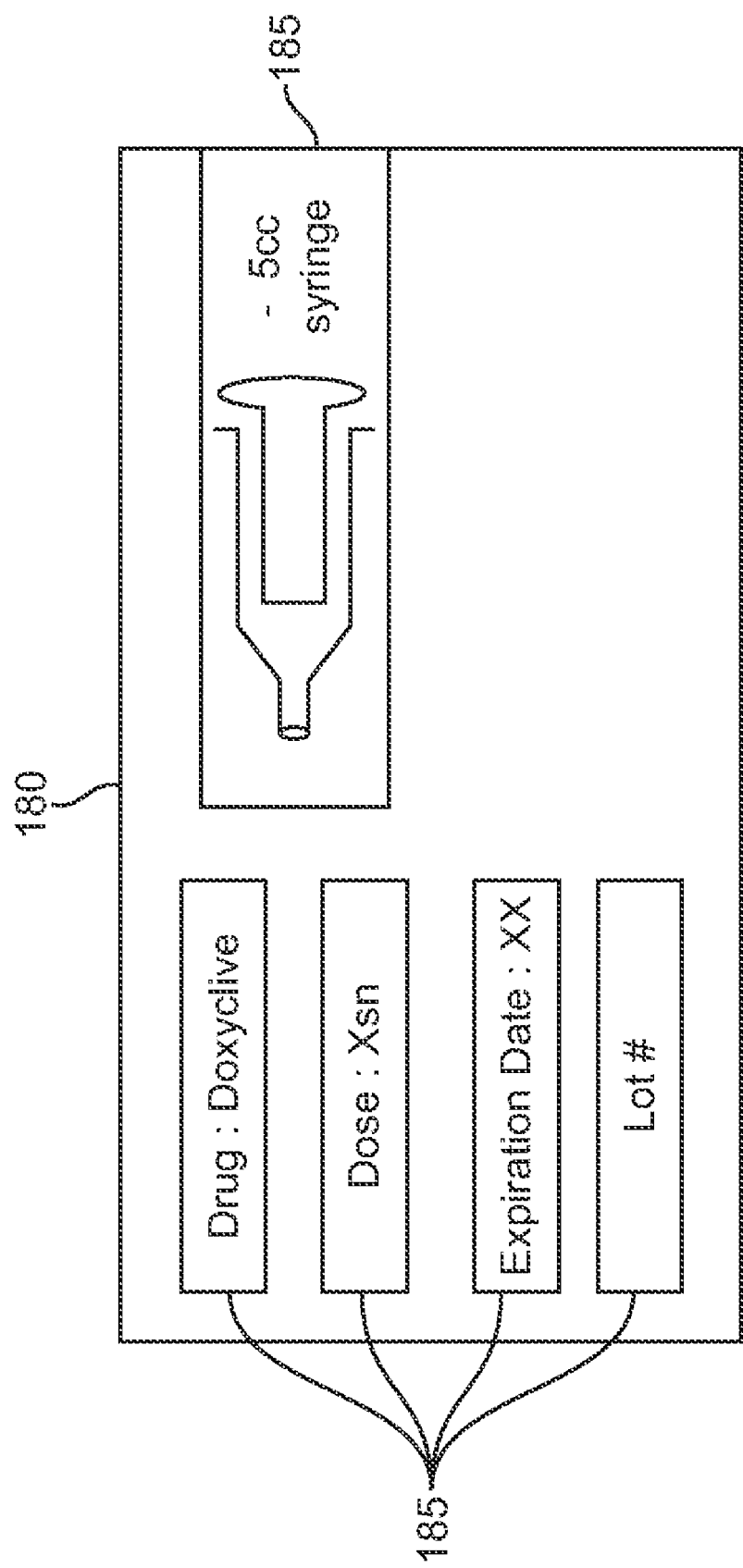
FIG. 9 is a side view illustrating an embodiment of packaging for use with embodiments of the syringe device and the skin penetrating device.

Referring now to FIGS. 8 and 9, another embodiment of the invention provides a syringe device 110 for delivery of a solid form therapeutic agent by injecting the agent through the skin into the muscle M or other subcutaneous tissue layer SCT. Similar to device 10, device 110 can be used to deliver a controlled amount of a solid form therapeutic agent into a subcutaneous tissue layer SCT so as to have that agent absorbed by body tissue fluids and into the blood stream to achieve a selectable plasma concentration over a selectable period of time. Also, the user can use syringe device 110 to make an injection into a selected tissue site TS in a similar manner as with the use of syringe containing a liquid therapeutic agent.

Device 110 comprises a syringe barrel 120 having a proximal and distal end 121 and 122 and a plunger 150 having proximal and distal end portions 151 and 152. Barrel 120 and plunger 150 are desirably fabricated from an inert clear sterilizable polymer known in the medical device arts and can include polyethylene, polypropylene, polyester, polycarbonate, PET, PMMA and copolymers thereof. The distal portion of the barrel 120 includes a thinner or needle section 160 which has a tissue piercing distal end 161 which in particular embodiments can comprise a beveled distal end 161b. Also, in particular embodiments, the plunger 150b can include a beveled distal end portion 152b with the angle of the bevel substantially matching that of beveled tissue piercing distal portion 161b. In use, this configuration serves to ensure that the entire dose of a therapeutic composition within barrel 120 is ejected when the plunger is fully depressed without having the plunger travel out of barrel including section 160.

Barrel 120 is packed with a premeasured dose 130 of a powderized or other solidly formed therapeutic agent composition 140 including at least one therapeutic agent 141 and one or more pharmaceutical excipients 142. Desirably, in these and related embodiments, excipients 142 include one or more glidants or other agents that enhance the flow of granular mixtures by reducing interparticle friction between particles of composition 140. Glidants 142 can include various biodegradable colloidal particles known in the art. They are desirably selected to ensure complete ejection of dose 130 from the syringe and reduce the force needed from plunger 150 to do so.

Dose 130 is desirably in powder form and can be micronized to a selected particle size or range of particle sizes configured to: i) facilitate complete ejection of dose 130 from the syringe barrel using minimal force; and ii) control the rate of absorption of the therapeutic agent by body tissue fluids and subsequent release into the blood stream. In various embodiments, the average particle size of dose 130/therapeutic composition 140 can range from 1 to 100 µm, with specific embodiments of 2, 5, 10, 20, 50 and 75 µm. The particle size can be selected depending upon the specific therapeutic agent and the desired absorption and release rate into the blood stream. Smaller particle sizes can be used for faster absorption and release rates. In particular embodiments, a mixture of particle sizes can be used to provide for multiple or staged release rates to allow for a rapid increase in plasma concentration by absorption of smaller particles and then the maintenance of that concentration by the slower absorption of larger size particles.

In various embodiments dose 130 can be protected by use of seals 170. In particular embodiments, a proximal and distal seals 171 and 172 can be placed on either side of dose 130. Seals 171 and 172 are desirably biodegradable and serve to protect dose 130 from oxidation and humidity and thus, can significantly extend the shelf life of dose 140 particular in high humidity environments. In some embodiments, only a distal seal 172 is included. Seals 171 and 172 can have a cylindrical like shape which can match the bevel of distal end 161 and or plunger end 152. They are desirably fabricated from a biodegradable material such as PGA or PGLA which degrade through hydrolytic or other degradation mechanism when exposed to the environment within body tissue.

The proximal end 151 of the plunger includes an end flange 135 for a user to push the plunger using the thumb or other finger. The barrel 120 also includes a flange 134 which engages end flange 135 and serves as a stop feature 134 to limit the travel of plunger 130. Additionally, a removable guard 136 is positioned between and coupled to barrel flange 134 and end flange 135. Guard 136 prevents the plunger 150 from being depressed and breaking seals 171 and 172. The guard 136 can be glued to flanges 134 and 135 using a low release force adhesive or coupled using solvent bonding or other polymer coupling method known in the art. This allows the user to easily pull or decouple the guard from flanges 134 and 135. The barrel 120 can also have volumetric measurement indicia 123 indicating the amount of dose 130 ejected from the barrel.

In many embodiments, device 110 is packaged in sterile packaging 180 as is shown in the embodiment of FIG. 9. Packaging 180 can have air and water vapor barrier properties that serve to extend the shelf life of dose 130. Such properties can be obtained by the use of various impermeable polymer materials known in the art. When such packaging 180 is combined with use of seals 171 and 172, significant periods of shelf life for dose 130 can be obtained including periods of one to three years or longer (e.g., five years or even longer). Such periods can be achieved by creation of essentially a double barrier seal, through the use of seals 171 and 172 and the seal provided by packaging 180. The packaging 180 can also include various indentifying indicia 185 identifying the therapeutic agent and its dosage. It can also be configured to be opened in a pealable or pull-apart manner using opposing layers in a similar fashion as a band-aid wrapper to allow for use of sterile technique in removing device 110 from the packaging. Various embodiments of packaging 180 can also be configured for use with device 10 and apparatus 60 as well.

For embodiments where the therapeutic agent is in solid form (which is much more concentrated than liquid form therapeutic agents. e.g., by factor of 10 or more) significant amounts of the therapeutic agent can be delivered by means of a single injection. Also, because the dose is in solid versus liquid form, its pharmacokinetics can be configured such that is not absorbed into the blood stream all at once but rather in a controlled manner configured to occur over a period of hours or even days so as to maintain a desired plasma concentration of the therapeutic agent over a selected period of time. In various embodiments, this combination of attributes can be configured to allow for an entire day's or even several days or a week's dose of a drug or other therapeutic agent to be delivered by a single injection, eliminating the need for multiple injections or oral doses as is the case for the treatment of many diseases and conditions (e.g., malaria which can require a week long dose of antibiotics; or diabetes, which can requires daily doses of insulin)

CONCLUSION

The foregoing description of various embodiments of the invention has been presented for purposes of illustration and description. It is not intended to limit the invention to the precise forms disclosed. Many modifications, variations and refinements will be apparent to practitioners skilled in the art. For example, the tissue penetrating element can modified in size, shape and dose of therapeutic agent for different tissue sites as well as for various pediatric applications.

Elements, characteristics, or acts from one embodiment can be readily recombined or substituted with one or more elements, characteristics or acts from other embodiments to form numerous additional embodiments within the scope of the invention. Moreover, elements that are shown or described as being combined with other elements, can, in various embodiments, exist as standalone elements. Hence, the scope of the present invention is not limited to the specifics of the described embodiments, but is instead limited solely by the appended claims.

What is claimed is:

1. A device for subcutaneous delivery of therapeutic agents in solid form, the device comprising:
    an elongated rigid shaft having a proximal and distal end; the rigidity of the shaft allowing the shaft to be advanced through skin using a sticking motion of the shaft towards the skin; and
    a skin penetrating element detachably coupled to the distal end of the shaft, the skin penetrating element having a proximal and distal end, at least a portion of the skin penetrating element comprising a solid form therapeutic agent composition;
    wherein the skin penetrating element has a shape configured to penetrate and lodge beneath the skin of a patient when inserted through the skin by force applied from the shaft during the sticking motion of the shaft and to detach from the shaft and remain when the shaft is pulled away from the skin;
    wherein a portion of the shaft that is extended from the skin of the patient when the skin penetrating element is lodged beneath the skin is structured to include a sub-portion, apart from a remainder of the shaft, that is grippable by fingers; and
    wherein the solid form therapeutic agent composition in the detached skin penetrating element is configured to dissolve in body tissue and be absorbed into the blood stream of the patient so as to produce a therapeutic effect in the patient; and
    wherein the shaft includes a depth control feature for controlling the depth of penetration of the skin penetrating element into tissue.

2. The device of claim 1, wherein the depth control feature is a stop feature for controlling the depth of penetration of the skin penetrating element into tissue.

3. The device of claim 1, wherein the skin penetrating element is configured to lodge and remain in a subcutaneous tissue layer.

4. The device of claim 3, wherein the subcutaneous tissue layer is a muscular layer.

5. The device of claim 1, wherein the proximal end of the skin penetrating element has an opening into which the shaft extends.

6. The device of claim 1, wherein the proximal end of the skin penetrating element has an elongated portion which extends into an opening on the distal end of the shaft.

7. The device of claim 1, wherein the proximal end of the skin penetrating element has a substantially flat shape configured to retain the skin penetrating element beneath or in the skin by a normal force applied to an overlying tissue layer when the shaft is pulled away from the skin.

8. The device of claim 1, wherein the skin penetrating element includes a retaining feature configured to retain the penetrating element beneath or in the skin when the shaft is pulled away from the skin.

9. The device of claim 1, wherein the therapeutic agent composition is configured to dissolve at a substantially constant rate.

10. The device of claim 1, wherein the detached skin penetrating element is configured to maintain a plasma concentration of the therapeutic agent above a threshold level for a period of time.

11. The device of claim 10, wherein the period of time is up to about 12 hours.

12. The device of claim 10, wherein the period of time is up to about 24 hours.

13. The device of claim 1, wherein the therapeutic agent composition comprises a micronized therapeutic agent.

14. The device of claim 13, wherein a particle size of the micronized therapeutic agent is selected to control an absorption rate of the therapeutic agent into the patient's bloodstream.

15. The device of claim 14, wherein the micronized therapeutic agent includes a mixture of particle sizes, the mixture including smaller particles selected to produce a faster rate of absorption of the therapeutic agent into the patient's bloodstream and larger particles selected to produce a slower rate of absorption so as to maintain a concentration of the therapeutic agent in the patient's bloodstream.

16. The device of claim 1, wherein the skin penetrating element has a substantially arrow head shape.

17. The device of claim 1, wherein the skin penetrating element comprises an outer layer at least partially surrounding an inner core of the therapeutic agent composition.

18. The device of claim 17, wherein the outer layer provides a barrier to gas and water vapor transmission to the inner core so as to extend a shelf life of the therapeutic agent composition.

19. The device of claim 17, wherein the outer layer has a greater hardness than the inner core so as to facilitate skin penetrating qualities of the skin penetrating element.

20. The device of claim 17, wherein at least a portion of the inner core comprises a liquid therapeutic agent composition.

21. The device of claim 20, wherein a section of a wall of the outer layer is configured to open as a result of a force from skin penetration so as to create a channel for release of the liquid therapeutic agent composition.

22. The device of claim 17, wherein a section of wall of the outer layer is configured to open as a result of a force from skin penetration so as to create a channel for entry of body fluids into the core and enhanced release of the therapeutic agent composition into tissue.

23. The device of claim 17, wherein the outer layer comprises a sugar compound.

24. The device of claim 1, wherein the therapeutic agent composition comprises an insulin compound.

25. The device of claim 1, wherein the therapeutic agent composition comprises a hormone effective for birth control.

26. The device of claim 25, wherein the hormone is at least one of estrogen or progesterone.

27. The device of claim 1, wherein the therapeutic agent composition comprises a vaccine.

28. The device of claim 27, wherein the vaccine comprises a battery of vaccines.

29. The device of claim 1, wherein the therapeutic agent composition comprises an antibiotic.

30. The device of claim 1, wherein the therapeutic agent composition comprises at least one antibiotic for the treatment of malaria.

31. The device of claim 1, wherein the therapeutic agent composition comprises epinephrine.

32. The device of claim 1, wherein the therapeutic agent composition comprises an antiemetic compound.

33. The device of claim 1, wherein the therapeutic agent composition comprises a pharmaceutical excepient.

34. The device of claim 33, wherein the pharmaceutical excepient comprises at least one of a binder, a preservative, an anti-oxidant or a disintegrant.

35. A device for subcutaneous delivery of therapeutic agents in solid form, the device comprising:
- an elongated rigid shaft having a proximal and distal end, the rigidity of the shaft allowing the shaft to be advanced through skin using a sticking motion of the shaft towards the skin; and
- a skin penetrating element detachably coupled to the distal end of the shaft, the skin penetrating element having a proximal and distal end, at least a portion of the skin penetrating element comprising a solid form therapeutic agent composition;
- wherein the skin penetrating element has a shape configured to penetrate and lodge beneath the skin of a patient when inserted through the skin by force applied from the shaft and to detach from the shaft and remain when the shaft is pulled away from the skin with a detachment force in a range of about 0.01 to 0.1 lbs;
- wherein a portion of the shaft that is extended from the skin of the patient when the skin penetrating element is lodged beneath the skin is structured to include a sub-portion, apart from a remainder of the shaft, that is grippable by fingers; and
- wherein the solid form therapeutic agent composition in the detached skin penetrating element is configured to dissolve in body tissue and be absorbed into the blood stream of the patient so as to produce a therapeutic effect in the patient; and wherein the shaft includes a depth control feature for controlling the depth of penetration of the skin penetrating element into tissue.

* * * * *